(12) United States Patent
Izzo et al.

(10) Patent No.: US 9,421,187 B2
(45) Date of Patent: Aug. 23, 2016

(54) PHYTOCANNABINOIDS FOR USE IN THE TREATMENT OF INTESTINAL INFLAMMATORY DISEASES

(71) Applicant: GW Pharma Limited, Salisbury (GB)

(72) Inventors: Angelo Antonio Izzo, Naples (IT); Francesca Borrelli, Naples (IT); Stephen Wright, Salisbury (GB)

(73) Assignee: GW Pharma Limited, Cambridge (GB)

( * ) Notice: Subject to any disclaimer, the term of this patent is extended or adjusted under 35 U.S.C. 154(b) by 0 days.

(21) Appl. No.: 14/359,192

(22) PCT Filed: Nov. 21, 2012

(86) PCT No.: PCT/GB2012/052886
§ 371 (c)(1),
(2) Date: May 19, 2014

(87) PCT Pub. No.: WO2013/076487
PCT Pub. Date: May 30, 2013

(65) Prior Publication Data
US 2014/0343136 A1 Nov. 20, 2014

(30) Foreign Application Priority Data
Nov. 21, 2011 (GB) .................................. 1120067.2

(51) Int. Cl.
*A61K 31/352* (2006.01)
*A61K 31/05* (2006.01)
*A61K 31/185* (2006.01)
*A61K 36/185* (2006.01)

(52) U.S. Cl.
CPC .............. *A61K 31/352* (2013.01); *A61K 31/05* (2013.01); *A61K 36/185* (2013.01)

(58) Field of Classification Search
CPC ............................ A61K 31/05; A61K 31/352
USPC ....................................................... 514/454
See application file for complete search history.

(56) References Cited

U.S. PATENT DOCUMENTS

2004/0192760 A1   9/2004   Whittle et al.
2010/0286098 A1   11/2010  Robson et al.

FOREIGN PATENT DOCUMENTS

| EP | 1 071 417 B1 | 2/2005 |
| EP | 1 559 423 A1 | 8/2005 |
| EP | 2 044 935 A1 | 4/2009 |
| EP | 1 542 657 B1 | 11/2011 |
| EP | 1 361 864 B1 | 12/2013 |
| GB | 2 450 493 A | 12/2008 |
| WO | WO 02/064109 A2 | 8/2002 |
| WO | WO 2004/016246 A1 | 2/2004 |
| WO | WO 2009/004302 A1 * | 1/2009 |

OTHER PUBLICATIONS

Bolognini et al. The plant cannabinoid delta-tetrahydrocannabivarin can decrease signs of inflammation and inflammatory pain in mice. British Journal of Pharmacology 2010, 160, pp. 677-687.*
Hundley et al. Nitric oxide-donating aspirin inhibits colon cancer cell growth via mitogen-activated protein kinase activation. The Journal of Pharamcology and Exmperimental Therapeutics. vol. 316, No. 1 pp. 25-34, Jan. 2006.*
Combined Search and Examination Report for GB1120067.2 mailed Mar. 12, 2012.
International Search Report and Written Opinion for PCT/GB2012/052886 mailed Jan. 10, 2013.
Written Opinion for PCT/GB2012/052886 mailed Nov. 26, 2013.
Borrelli et al., Cannabidiol, a safe and non-psychotropic ingredient of the marijuana plant *Cannabis sativa*, is protective in a murine model of colitis. J Mol Med (Berl). Nov. 2009;87(11):1111-21. doi: 10.1007/s00109-009-0512-x. Epub Aug. 20, 2009.
Colombel et al., Adalimumab for maintenance of clinical response and remission in patients with Crohn's disease: the Charm trial. Gastroenterology. Jan. 2007;132(1):52-65. Epub Nov. 29, 2006.
Di Carlo et al., Cannabinoids for gastrointestinal diseases: potential therapeutic applications. Expert Opin Investig Drugs. Jan. 2003;12(1):39-49.
Fride et al., Peripheral, but not central effects of cannabidiol derivatives: mediation by CB(1) and unidentified receptors. Neuropharmacology. Jun. 2005;48(8):1117-29. Epub Apr. 26, 2005.
Izzo et al., Cannabinoids in intestinal inflammation and cancer. Pharmacol Res. Aug. 2009;60(2):117-25. doi: 10.1016/j.phrs.2009.03.008. Epub Mar. 18, 2009.
Kanai et al., Extracorporeal elimination of TNF-alpha-producing CD14(dull)CD16(+) monocytes in leukocytapheresis therapy for ulcerative colitis. Inflamm Bowel Dis. Mar. 2007;13(3):284-90.
Massa et al., Endocannabinoids and the gastrointestinal tract. J Endocrinol Invest. 2006;29(3 Suppl):47-57.
Nakase et al., Development of an oral drug delivery system targeting immune-regulating cells in experimental inflammatory bowel disease: a new therapeutic strategy. J Pharmacol Exp Ther. Jan. 2000;292(1):15-21.
Pertwee, The diverse CB1 and CB2 receptor pharmacology of three plant cannabinoids: delta9-tetrahydrocannabinol, cannabidiol and delta9-tetrahydrocannabivarin. Br J Pharmacol. Jan. 2008;153(2):199-215. Epub Sep. 10, 2007.
Rossi et al., The 5-lipoxygenase inhibitor, zileuton, suppresses prostaglandin biosynthesis by inhibition of arachidonic acid release in macrophages. Br J Pharmacol. Oct. 2010;161(3):555-70. doi:10.1111/j.1476-5381.2010.00930.x.
Schenk et al., TREM-1—expressing intestinal macrophages crucially amplify chronic inflammation in experimental colitis and inflammatory bowel diseases. J Clin Invest. Oct. 2007;117(10):3097-106.

* cited by examiner

*Primary Examiner* — Jennifer M Kim
(74) *Attorney, Agent, or Firm* — Wolf, Greenfield & Sacks, P.C.

(57) ABSTRACT

The present invention relates to one or more of the phytocannabinoids tetrahydrocannabivarin (THCV); cannabigerol (CBG); cannabichromene (CBC); and cannabidivarin (CBDV) for use in the treatment of intestinal inflammatory diseases. Preferably the intestinal inflammatory disease is either ulcerative colitis or Crohn's disease.

9 Claims, 11 Drawing Sheets

Effect of isolated cannabidivarin (CBDV), cannabichromene (CBC), cannabigerol (CBG) and tetrahydrocannabivarin (THCV) on mouse peritoneal macrophage viability Effect of cannabidivarin (CBDV), cannabichromene (CBC), cannabigerol (CBG) and tetrahydrocannabivarin (THCV) botanical drug substances (BDS) on mouse peritoneal macrophage viability Effect of isolated cannabidivarin (CBDV), cannabichromene (CBC), cannabigerol (CBG) and tetrahydrocannabivarin (THCV) on nitrite levels in mouse peritoneal macrophages Effect of cannabidivarin (CBDV), cannabichromene (CBC), cannabigerol (CBG) and tetrahydrocannabivarin (THCV) botanical drug substances (BDS) on nitrite levels in mouse peritoneal macrophages Effect of cannabigerol (CBG) on body weight in DNBS-induced colitis mice A (preventative treatment)

B (curative treatment)

Effect of cannabigerol (CBG) on colon weight : length ratio in DNBS-induced colitis mice

A (preventive treatment)

B (curative treatment)

Effect of cannabichromene (CBC) on body weight in DNBS-induced colitis mice

A (preventative treatment)

B (curative treatment)

Effect of cannabichromene (CBC) on colon weight : length ratio in DNBS-induced colitis mice A (preventative treatment)

B (curative treatment)

Effect of tetrahydrocannabivarin (THCV) on bodyweight in DNBS-induced colitis mice Effect of tetrahydrocannabivarin (THCV) on the colon weight : length ratio in DNBS-induced colitis mice Effect of cannabichromene (CBC), cannabigerol (CBG) and tetrahydrocannabivarin (THCV) on iNOS expression in DNBS-induced colitis mice

PHYTOCANNABINOIDS FOR USE IN THE TREATMENT OF INTESTINAL INFLAMMATORY DISEASES

RELATED APPLICATION

This application is a national stage filing under 35 U.S.C. §371 of international application PCT/GB2012/052886, filed Nov. 21, 2012, which was published under PCT Article 21(2) in English.

The present invention relates to one or more of the phytocannabinoids tetrahydrocannabivarin (THCV); cannabigerol (CBG); cannabichromene (CBC); and cannabidivarin (CBDV) for use in the treatment of intestinal inflammatory diseases. Preferably the intestinal inflammatory disease is either ulcerative colitis or Crohn's disease.

DEFINITIONS

In this specification the following terms are used and are intended to have the following meanings/definitions:

"Cannabinoids" are a group of compounds including the endocannabinoids, the phytocannabinoids and those which are neither endocannabinoids or phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and rimonabant.

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 50% of the phytocannabinoid-containing fraction, more preferably still greater than 55% of the phytocannabinoid-containing fraction, and more preferably still greater than 60% through 65%, 70%, 75%, 80%, 85%, 90% and 95% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 5% (w/w) of the total extract, and most preferably the minor phytocannabinoid is present in an amount less than 2% (w/w) of the total extract.

The term "consisting essentially of" is limited to the phytocannabinoids which are specified, it does not exclude non-cannabinoid components that may also be present.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

The "principle monoterpene/s" in a BDS is the monoterpene that is present in an amount that is higher than that of the other monoterpenes. Preferably the principle monoterpene/s is present in an amount greater than 20% (w/w) of the total terpene content. More preferably the principle monoterpene is present in an amount greater than 30% (w/w) of the total terpene content, more preferably still greater than 40% (w/w) of the total terpene content, and more preferably still greater than 50% (w/w) of the total terpene content. The principle monoterpene is preferably a myrcene or pinene. In some cases there may be two principle monoterpenes. Where this is the case the principle monoterpenes are preferably a pinene and/or a myrcene.

The "principle sesquiterpene" in a BDS is the sesquiterpene that is present in an amount that is higher than all the other sesquiterpenes. Preferably the principle sesquiterpene is present in an amount greater than 20% (w/w) of the total terpene content, more preferably still greater than 30% (w/w) of the total terpene content. The principle sesquiterpene is preferably a caryophyllene and/or a humulene.

The sesquiterpene components may have a "secondary sesquiterpene". The secondary sesquiterpene is preferably a pinene, which is preferably present at an amount greater than 5% (w/w) of the total terpene content, more preferably the secondary sesquiterpene is present at an amount greater than 10% (w/w) of the total terpene content.

The secondary sesquiterpene is preferably a humulene which is preferably present at an amount greater than 5% (w/w) of the total terpene content, more preferably the secondary sesquiterpene is present at an amount greater than 10% (w/w) of the total terpene content.

Alternatively botanical extracts may be prepared by introducing isolated phytocannabinoids or their synthetic equivalent into a non-cannabinoid plant fraction as can be obtained from a zero cannabinoid plant or one or more non-cannabinoid components found in the cannabis plant such as terpenes.

The structure of the phytocannabinoids THCV, CBG, CBC and CBDV are shown below, the structure of CBD is shown for comparison:

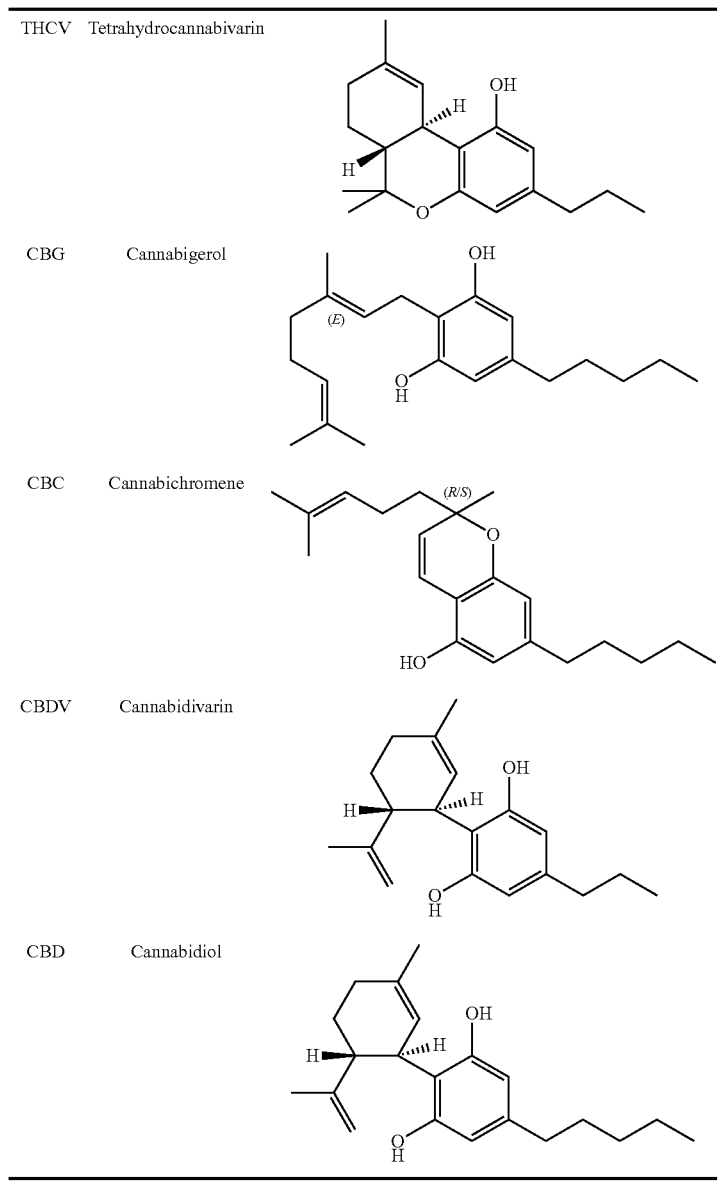

60

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Where a synthetic phytocannabinoid is used the term is intended to include compounds, metabolites or derivatives thereof, and pharmaceutically acceptable salts of such compounds.

The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

For the purpose of this invention the term "treatment" refers to reducing or preventing inflammation in the intestine and a therapeutically effective amount is an amount that achieves this aim.

The term "preventative treatment" is intended to refer to pre-treatment with an agent that is able to prevent an inflammatory response in the intestines in subjects who are susceptible to diseases associated with inflammation of the intestines. Such a preventative treatment is associated with a protective effect which may be due to immunomodulation.

The term "curative treatment" is intended to refer to treatment with an agent that is able to stop or substantially slow down the inflammatory response in the intestines in subjects who are suffering from diseases associated with inflammation of the intestines. When a curative effect is seen the phytocannabinoids are working to directly target the inflammation resulting in an anti-inflammatory effect.

BACKGROUND TO THE INVENTION

Intestinal inflammatory disease is the term used to describe chronic diseases that cause inflammation of the intestines. Diseases such as ulcerative colitis and Crohn's disease are examples of intestinal inflammatory disease. Other diseases which affect the intestines such as irritable bowel disease may be caused by inflammation in part of the intestines.

Ulcerative colitis is an inflammatory disease of the colon. In ulcerative colitis, the lining of the intestinal wall reddens and swells and develops ulcers. The condition is often most severe in the rectal area, which can cause frequent diarrhoea. Additionally mucus and blood may appear in the stool if the lining of the colon is damaged.

Crohn's disease may affect any part of the digestive system, from the mouth to the anus, but it is most common in the lower part of the small bowel or the first part of the large bowel. It often affects more than one part of the bowel leaving normal, unaffected areas in between.

Crohn's disease is a chronic relapsing inflammatory disorder of the gastrointestinal (GI) tract occurring worldwide, most notably in North America and Europe with an incidence of 2-6 per 100,000 per year and a prevalence of 60-80 per 100,000. The onset of disease can occur in any age group but is more common in young adults. Crohn's disease is characterised by mucosal membrane inflammation affecting any part of the GI tract, with the terminal ileum (35%), ileocaecal region (40%) and colon (20%) generally being the most affected areas.

Crohn's disease patients have an increased blood flow in the wall of the bowel; this causes inflammation and ulceration, which extends to the deepest layers of the bowel.

The exact cause of Crohn's disease is not known, but it is thought that the body's immune system overreacts to a virus or bacterium, causing on-going inflammation in the bowel. The disease often tends to run in families.

Crohn's disease is usually a life-long condition, with alternating flare-ups of symptoms and periods of remission. The symptoms include: diarrhoea, up to 10 or 20 times a day; pain, anywhere in the abdomen, and is often described as cramping or colicky. The abdomen may be sore to the touch and swollen; loss of appetite; weight loss; fever; rectal bleeding; anaemia; fissures and abscesses in the anal area.

During a flare-up of symptoms problems in other areas of the body may also occur, such as mouth ulcers, joint pain, eye inflammation, rashes and ulcers on the skin.

With chronic Crohn's disease, severe inflammation may cause complications to develop. This includes a fistula, which is an abnormal connection between the bowel and a neighbouring part of the body, such as the bladder, vagina, or another loop of bowel. Fistulas may lead to recurrent infections of the urinary or genital tracts. Other complications include an abscess (collection of pus) inside the abdomen or a stricture, a narrowing of the bowel caused by scar tissue that can obstruct the passage of material through the bowel. It is also known that patients who have had Crohn's disease for 8 to 10 years are at an increased risk of bowel cancer.

There is no cure for Crohn's disease. Symptoms can be improved with dietary changes, drugs or surgery, or a combination of these.

Medicines to reduce inflammation such as corticosteroids are often used in Crohn's disease along with medicines that suppress the immune system. Anti-diarrhoea medicines, antibiotics and painkillers may also be used during flare-ups.

Existing therapies currently available for use in the treatment of acute active Crohn's disease, particularly corticosteroids, are not universally effective or well tolerated by all patients and/or may not be cost-effective in the long-term. In addition, approximately 45% of patients cannot discontinue corticosteroid treatment without an exacerbation of their disease and consequently, many patients can become tolerant to such drugs although, this is more evident in moderate to severe disease.

Many people with Crohn's disease require surgical treatment at some time to treat complications such as anal abscesses, or fistulae, to remove areas of narrowed, non-functioning bowel, or when drugs are not controlling the disease.

The phytocannabinoid CBD has been ascribed as an anti-inflammatory agent (Fride et al. (2005) and Di Carlo and Izzo (2003).

Massa and Monory (2006) describes the use of the endocannabinoids as natural protectants in inflammatory and gastrointestinal disorders.

Cannabidiol (CBD) was shown to exert an anti-inflammatory effect in the DNBS model of intestinal bowel disease in mice (Borrelli et al. 2009).

Furthermore EP1071417 describes the use of pure cannabidiol. The pure CBD is thought to be useful as an anti-inflammatory agent and much data is provided for its use as a treatment for rheumatoid arthritis.

The applications EP1361864 and EP1542657 suggest that the use of a broad ratio CBD:THC (19:1) product might be useful in the treatment of inflammatory bowel disease.

The application WO 2009/004302 describes a combination of the cannabinoids tetrahydrocannabinol (THC) and cannabidiol (CBD) may be useful in the treatment of an inflammatory bowel disease. The ratio of THC to CBD used is between 1:1 to 1:2.

Intestinal inflammatory disease affects millions of individuals and although major advances have been made in respect to treatment, many patients still receive suboptimal treatment (Colombel et al. 2008).

The application WO 2009/004302 describes a CBD extract for use in the treatment of intestinal inflammatory disorders, the application goes on to disclose that the CBD extract comprises minor amounts of other cannabinoids including CBG, CBC and CBDV.

The patent EP 2,044,935 describes an extract from cannabis that might be useful in the treatment of gastrointestinal inflammatory diseases. The extract may comprise CBG or CBD.

The application WO 02/064109 describes that extracts of THC and CBD may comprise minor amounts of other cannabinoids.

The patent EP 1,559,423 describes the use of acid cannabinoids in inflammatory diseases.

The application GB 2450493 describes the use of CBG in the treatment of many different diseases or conditions dependent on CBG's ability to agonise the CB1 and CB2 receptors.

It is an object of the present invention to provide a new treatment option for intestinal inflammatory diseases, as there is clearly an unmet need for new medications which are able to successfully control these diseases.

It has been observed that the phytocannabinoids tetrahydrocannabivarin (THCV); cannabigerol (CBG); cannabichromene (CBC); and cannabidivarin (CBDV) are effective agents in reducing intestinal inflammation. Such compounds might have utility in the treatment of inflammatory diseases of the intestines such as ulcerative colitis and Crohn's disease.

BRIEF SUMMARY OF THE DISCLOSURE

In accordance with a first aspect of the present invention there is provided one or more of the phytocannabinoids tetrahydrocannabivarin (THCV); cannabigerol (CBG); cannabichromene (CBC); and/or cannabidivarin (CBDV) for use in the treatment of intestinal inflammatory diseases.

In one embodiment the intestinal inflammatory disease is ulcerative colitis. In a further embodiment the intestinal inflammatory disease is Crohn's disease.

Preferably the one or phytocannabinoid are used as a preventative treatment of intestinal inflammatory diseases.

Alternatively the one or more phytocannabinoids are used as a curative treatment of intestinal inflammatory diseases.

In one embodiment the one or more phytocannabinoids are a synthetic cannabinoid or an isolated phytocannabinoid.

In an alternative embodiment the one or more of the phytocannabinoids are present as an extract from a cannabis plant. Preferably the extract from a cannabis plant is a botanical drug substance (BDS).

A typical THCV BDS is as described in Tables 1.1 and 1.2 below:

TABLE 1.1

Tetrahydrocannabivarin BDS amount in total and range

| THCV BDS | Amount (% w/w) | Range (±10%) | Range (±25%) | Range (±50%) |
| --- | --- | --- | --- | --- |
| CBGV | 0.15 | 0.14-0.17 | 0.11-0.19 | 0.07-0.23 |
| CBNV | 1.30 | 1.2-1.40 | 1.00-1.60 | 0.65-1.95 |
| THCV | 64.49 | 58.04-70.94 | 48.37-80.61 | 32.25-96.74 |
| CBCV | 0.65 | 0.59-0.72 | 0.49-0.81 | 0.33-0.98 |
| THC-C4 | 0.82 | 0.74-0.90 | 0.62-1.03 | 0.41-1.23 |
| CBN | 0.15 | 0.14-0.17 | 0.11-0.19 | 0.07-0.23 |
| THCVA | 0.36 | 0.32-0.40 | 0.27-0.45 | 0.18-0.54 |
| THC | 13.43 | 12.09-14.77 | 10.07-16.79 | 7.72-20.15 |
| Unknowns | 0.58 | 0.52-0.64 | 0.44-0.73 | 0.29-0.87 |
| Total Cannabinoids | 81.93 | | | |
| Total Non-cannabinoids | 18.07 | | | |

The total phytocannabinoid containing fraction of THCV BDS comprises approximately 74-90% (w/w) of the total BDS.

TABLE 1.2

Tetrahydrocannabivarin BDS by percentage cannabinoid

| THCV BDS | Amount (% of total cannabinoid) |
| --- | --- |
| CBGV | 0.18 |
| CBNV | 1.59 |
| THCV | 78.71 |
| CBCV | 0.79 |
| THC-C4 | 1.00 |
| CBN | 0.18 |
| THCVA | 0.44 |
| THC | 16.39 |
| Unknowns | 0.71 |

The amount of the principle phytocannabinoid in the THCV BDS as a percentage of the phytocannabinoid containing fraction is approximately 71-87% (w/w). The THCV BDS also has a secondary cannabinoid THC which is present at approximately 14.8-18% (w/w) of the phytocannabinoid containing fraction.

A typical CBG BDS is as described in Tables 1.3 and 1.4 below:

TABLE 1.3

Cannabigerol BDS amount in total and range

| CBG BDS | Amount (% w/w) | Range (±10%) | Range (±25%) | Range (±50%) |
| --- | --- | --- | --- | --- |
| CBGV | 0.33 | 0.30-0.36 | 0.25-0.41 | 0.17-0.50 |
| CBG | 66.96 | 60.3-73.7 | 50.2-83.7 | 33.5-100.0 |
| THC | 0.03 | 0.027-0.033 | 0.023-0.038 | 0.015-0.045 |
| CBC | 0.07 | 0.06-0.08 | 0.05-0.09 | 0.035-0.105 |
| CBG (related substance) | 1.35 | 1.22-1.49 | 1.01-1.69 | 0.68-2.03 |
| Total Cannabinoids | 68.74 | | | |
| Total Non-cannabinoids | 31.26 | | | |

The total phytocannabinoid containing fraction of CBG BDS comprises approximately 61-75% (w/w) of the total BDS.

TABLE 1.4

Cannabigerol BDS by percentage cannabinoid

| CBG BDS | Amount (% of total cannabinoid) |
|---|---|
| CBGV | 0.48 |
| CBG | 97.41 |
| THC | 0.04 |
| CBC | 0.10 |
| CBG (related substance) | 1.96 |

The amount of the principle phytocannabinoid in the CBG BDS as a percentage of the phytocannabinoid containing fraction is approximately 88-100% (w/w).

A typical CBC BDS is as described in Tables 1.5 and 1.6 below:

TABLE 1.5

Cannabichromene BDS amount in total and range

| CBC BDS | Amount (% w/w) | Range (±10%) | Range (±25%) | Range (±50%) |
|---|---|---|---|---|
| CBG | 0.91 | 0.82-1.00 | 0.68-1.14 | 0.46-1.37 |
| CBD | 3.96 | 3.56-4.36 | 2.97-4.95 | 1.98-5.94 |
| CBCV | 0.74 | 0.67-0.81 | 0.56-0.93 | 0.37-1.11 |
| THC | 1.76 | 1.58-1.94 | 1.32-2.20 | 0.88-2.64 |
| CBC (related substances) | 0.13 | 0.12-0.14 | 0.10-0.16 | 0.07-0.20 |
| CBC | 42.95 | 38.65-47.25 | 32.22-56.69 | 21.48-64.43 |
| CBCA | 0.56 | 0.50-0.62 | 0.42-0.70 | 0.28-0.84 |
| CBL | 3.54 | 3.19-3.89 | 2.67-4.43 | 1.77-5.31 |
| Total Cannabinoids | 54.55 | | | |
| Total Non-cannabinoids | 45.45 | | | |

The total phytocannabinoid containing fraction of CBC BDS comprises approximately 49-60% (w/w) of the total BDS.

TABLE 1.6

Cannabichromene BDS by percentage cannabinoid

| CBC BDS | Amount (% of total cannabinoid) |
|---|---|
| CBG | 1.67 |
| CBD | 7.26 |
| CBCV | 1.36 |
| THC | 3.23 |
| CBC (related substances) | 0.24 |
| CBC | 78.74 |
| CBCA | 1.03 |
| CBL | 6.49 |

The amount of the principle phytocannabinoid in the CBC BDS as a percentage of the phytocannabinoid containing fraction is approximately 71-87% (w/w). The CBC BDS also has two secondary cannabinoids: CBD which is present at approximately 6.5-8% (w/w) of the phytocannabinoid containing fraction and CBL which is present at approximately 5.8-7.1% (w/w) of the phytocannabinoid containing fraction.

A typical CBDV BDS is as described in Tables 1.7 and 1.8 below:

TABLE 1.7

Cannabidivarin BDS amount in total and range

| CBDV BDS | Amount (% w/w) | Range (±10%) | Range (±25%) | Range (±50%) |
|---|---|---|---|---|
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| THCV | 3.06 | 2.75-6.12 | 2.30-3.83 | 1.53-4.59 |
| CBCV | 4.35 | 3.92-4.79 | 3.26-5.44 | 2.18-6.53 |
| THC | 0.88 | 0.79-0.97 | 0.66-1.10 | 0.44-1.32 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 71.11 | | | |
| Total Non-cannabinoids | 28.89 | | | |

The total phytocannabinoid containing fraction of CBDV BDS comprises approximately 64-78% (w/w) of the total BDS.

TABLE 2.6.2

| CBDV BDS | Amount (% of total cannabinoid) |
| --- | --- |
| Cannabidivarin BDS by percentage cannabinoid | |
| CBDVA | 0.20 |
| CBDV | 57.92 |
| CBDA | 0.10 |
| CBG | 0.83 |
| CBD | 24.89 |
| THCV | 4.30 |
| CBCV | 6.12 |
| THC | 1.24 |
| CBDV (related substances) | 3.09 |
| CBC | 1.31 |

The amount of the principle phytocannabinoid in the CBDV BDS as a percentage of the phytocannabinoid containing fraction is approximately 52-64% (w/w). The CBDV BDS also has two secondary cannabinoids: CBD which is present at approximately 22.4-27.4% (w/w) of the phytocannabinoid containing fraction and CBCV which is present at approximately 5.5-6.7% (w/w) of the phytocannabinoid containing fraction.

The one or more phytocannabinoids will be present in a therapeutically acceptable amount, which may, for example, be between 1 mg and 2000 mg.

The human dose equivalent (HED) can be estimated using the following formula:

$$HED = \text{Animal dose (mg/kg) multiplied by } \frac{\text{Animal } K_m}{\text{Human } K_m}$$

The $K_m$ for a mouse is 3 and the $K_m$ for a human is 37.

In accordance with a second aspect of the present invention there is provided the use of one or more of the phytocannabinoid tetrahydrocannabivarin (THCV); cannabigerol (CBG); cannabichromene (CBC); and/or cannabidivarin (CBDV) in the manufacture of a medicament for use in the treatment of intestinal inflammatory diseases.

In accordance with a third aspect of the present invention there is provided a method of treating a patient suffering from intestinal inflammatory disease comprising administering a therapeutically effective amount of one or more of the phytocannabinoids tetrahydrocannabivarin (THCV); cannabigerol (CBG); cannabichromene (CBC); and/or cannabidivarin (CBDV) to the patient.

BRIEF DESCRIPTION OF THE DRAWINGS

Embodiments of the invention are further described hereinafter with reference to the accompanying drawings, in which.

DETAILED DESCRIPTION

Figure 1:
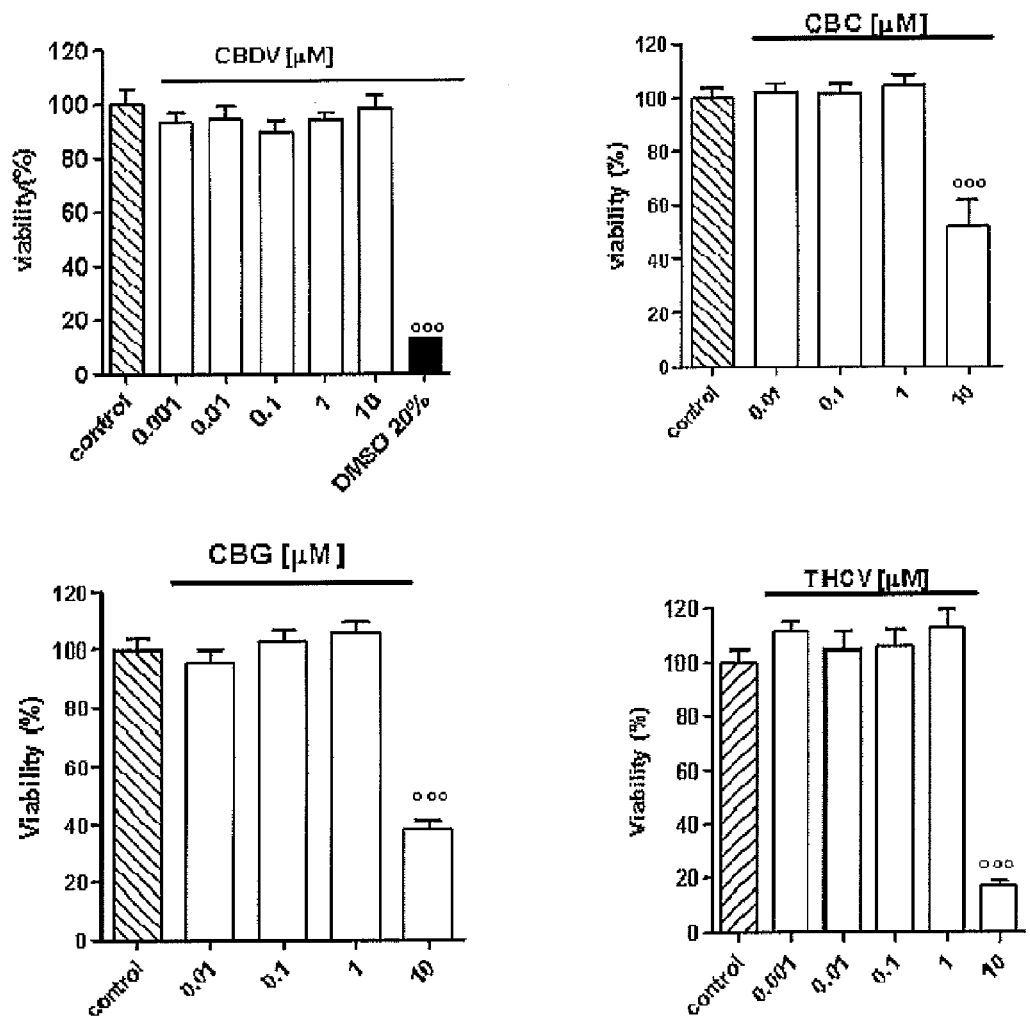
FIG. 1 shows the effect of isolated cannabidivarin (CBDV), cannabichromene (CBC), cannabigerol (CBG) and tetrahydrocannabivarin (THCV) on mouse peritoneal macrophage viability.

The Examples below were designed to examine whether the phytocannabinoids tetrahydrocannabivarin (THCV), cannabigerol (CBG), cannabichromene (CBC) and/or cannabidivarin (CBDV) were able to reduce inflammation in in vitro and in vivo models of intestinal inflammatory disease.

It is well established that macrophages are deeply involved in maintaining intestinal homeostasis and negatively regulate excess immune responses evoked by external insults (Schenk and Mueller, 2007). Studies have suggested that macrophage-targeting treatment ameliorates colonic inflammation in experimental colitis models (Nakase et al. 2000; Kanai et al. 2006). Thus, the regulation of abnormal responses of macrophages appears to be a promising therapeutic approach for the treatment of intestinal inflammatory disease.

Example 1 evaluates the potential of the phytocannabinoids THCV, CBG, CBC and CBDV in intestinal inflammatory disease by their effect on mouse peritoneal macrophages.

Example 2 investigates the effect of CBG, CBC and THCV in an in vivo model of colitis.

EXAMPLE 1

Effect of Tetrahydrocannabivarin (THCV), Cannabigerol (CBG), Cannabichromene (CBC) and Cannabidivarin (CBDV) on Mouse Peritoneal Macrophages Materials and Methods Test Articles:

The following isolated phytocannabinoids and their corresponding botanical drug substances (BDS) were evaluated: THCV, CBG, CBC and CBDV. These compounds were dissolved in DMSO or ethanol, which, at the concentration used (0.01%), had no effect on the responses under study.

Isolation of Mouse Peritoneal Macrophages:

Peritoneal macrophages were obtained from mice as previously described by Rossi et al. (Rossi et al. 2010). Briefly, to evoke the production of peritoneal exudates rich in macrophages, mice were injected intraperitoneally (i.p.) with 1 ml of 10% sterile thioglycollate (Sigma, Milan, Italy). After 4 days, mice were euthanized and peritoneal macrophages were collected and seeded in appropriate plates for performing in vitro experiments.

Cell Culture:

Peritoneal macrophages were cultured in Dulbecco's modified Eagle's medium (DMEM) supplemented with 10% fetal bovine serum. The inflammatory response in peritoneal macrophages was induced by lipopolysaccharide (LPS) from *Escherichia coli* serotype 0111:B4 (1 µg/ml). The response in macrophages was measured after 18 h LPS incubation.

Cytotoxicity Assays:

Cell viability was assessed by evaluating cell respiration as well as neutral red (NR) uptake. Cell respiration was assessed by the mitochondrial-dependent reduction of 3-(4,5-dimethylthiazol-2-yl)-2,5-diphenyltetrazolium bromide (MTT) to formazan. After incubation with one of the phytocannabinoids for 24 hours, macrophages ($1\times10^5$ cells per well seeded in a 96-well plate) were incubated with MTT (250 µg/ml) for 1 h.

The extent of reduction of MTT to formazan was quantitated by measuring the optical density at 490 nm (iMark™ microplate assorbance reader, BioRad).

For the Neutral Red (NR) uptake assay, after incubation with test article for 24 hours, macrophages ($1\times10^5$ cells perwell seeded in a 96-well plate) were incubated with neutral red (NR) dye solution (50 µg/ml) for 3 hours, and then lysed by adding 1% acetic acid. The absorbance was read at 532 nm (iMark™ microplate assorbance reader, BioRad).

Nitrites Measurement:

Nitrites, stable metabolites of NO, were measured in macrophages medium as previously described [19]. Macrophages ($5\times10^5$ cells per well seeded in a 24-well plate) were incubated with test article (0.1-10 pM) for 30 min, and subsequently with LPS (1 µg/ml) for 18 hours. After reduction of nitrates to nitrites by cadmium, cell supernatants were incubated with DAN (50 µg/ml) for 7 min and the reaction stopped with 2.8 N NaOH, nitrites levels were measured using a fluorescent microplate reader (LS55 Luminescence Spectrometer, Perkin-Elmer Instruments, excitation-emission wavelengths of 365-450 nm).

Statistical Analysis:

Results are expressed as mean±SEM and analysed with the student's t-test or one-way ANOVA followed by a Turkey-Kramer multiple comparisons test. A P value less than 0.05 was regarded as significant.

Results

Cytotoxicity:

Results on cytotoxicity of the isolated phytocannabinoids are shown in FIG. 1. It can be observed that isolated CBDV was not cytotoxic up to 10 µM. In contrast isolated THCV, CBG, and CBC significantly reduced cell viability at the highest 10 µM concentration.

Figure 2:
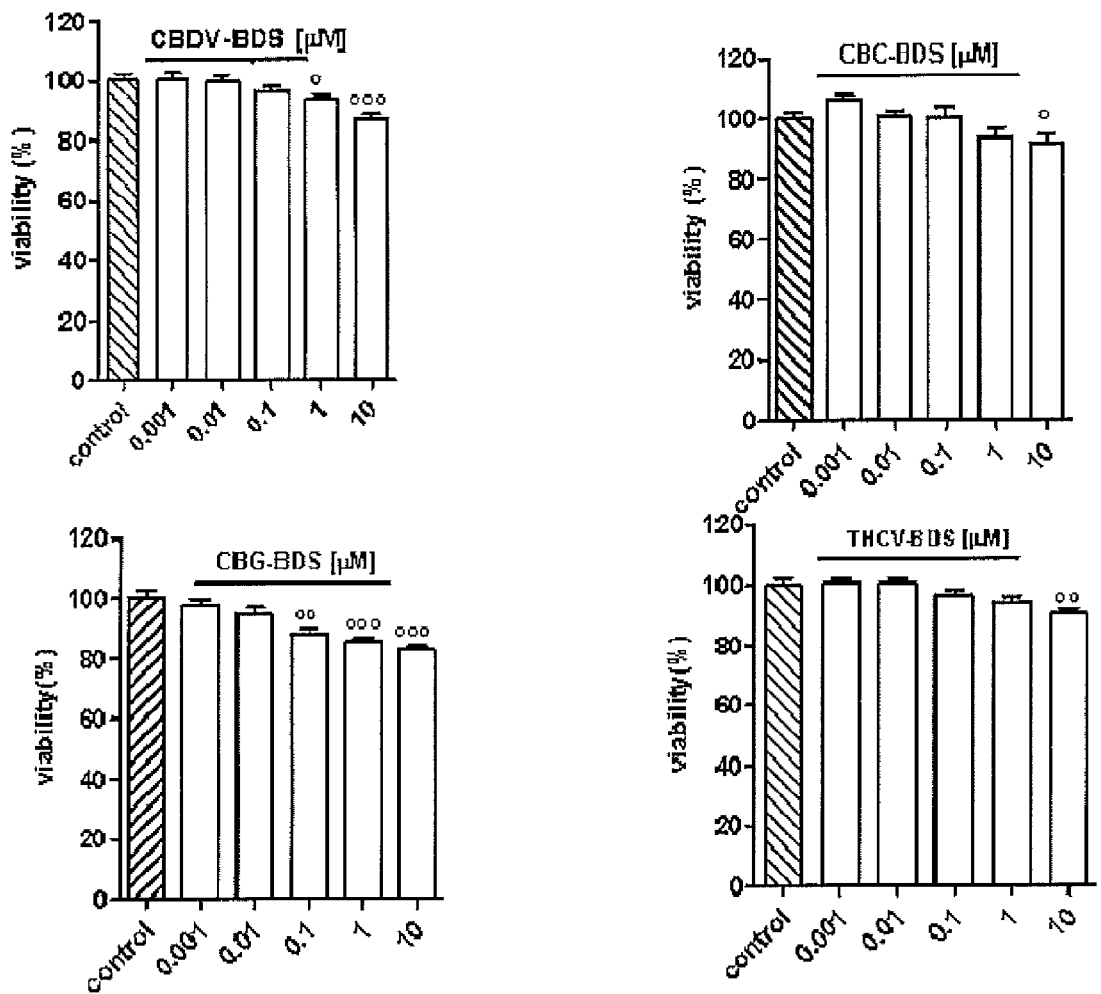
FIG. 2 shows the effect of cannabidivarin (CBDV), cannabichromene (CBC), cannabigerol (CBG) and tetrahydrocannabivarin (THCV) botanical drug substances (BDS) on mouse peritoneal macrophage viability.

FIG. 2 describes the cytotoxicity of the phytocannabinoid BDS examined. It can be seen that all of the phytocannabinoid BDS reduced macrophage viability in the 0.1-10 µM range.

Specifically, CBDV BDS was cytotoxic at the concentrations of 1 and 10 µM, CBC-BDS and THCV-BDS at the higher concentration tested (10 µM), while CBG-BDS significantly reduced macrophage viability starting from the 0.1 µM concentration.

Figure 3:
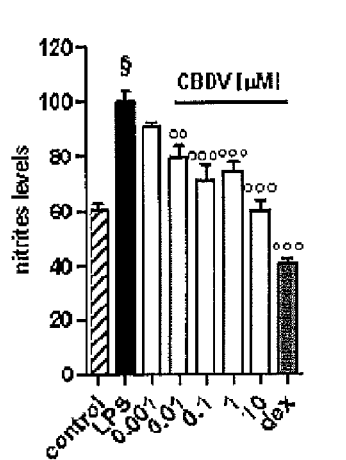
FIG. 3 shows the effect of isolated cannabidivarin (CBDV), cannabichromene (CBC), cannabigerol (CBG) and tetrahydrocannabivarin (THCV) on nitrite levels in mouse peritoneal macrophages.
Figure 3:
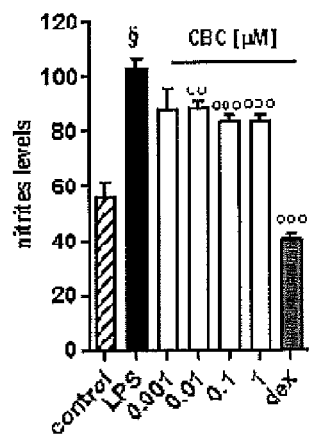
Figure 3:
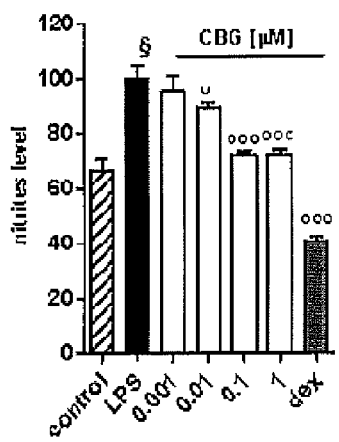
Figure 3:
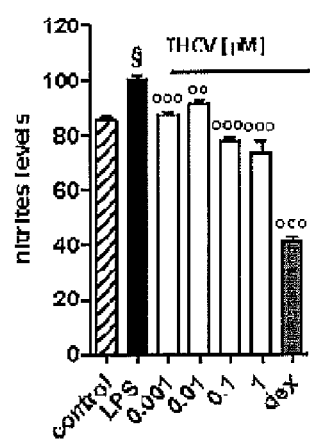
Figure 4:
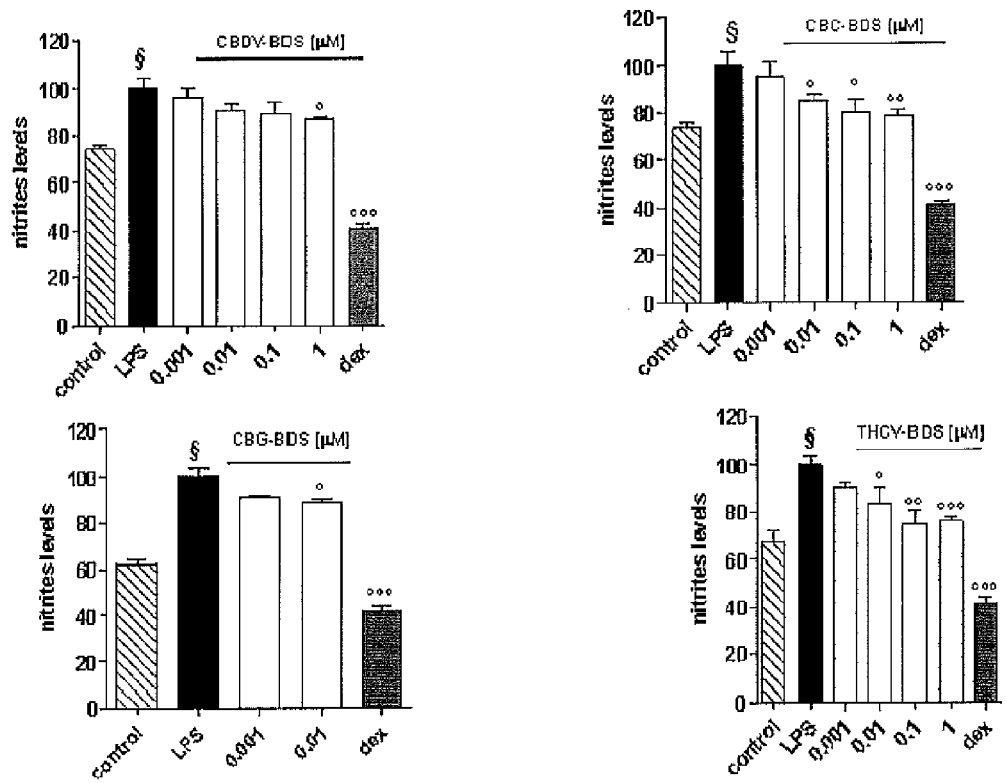
FIG. 4 shows the effect of cannabidivarin (CBDV), cannabichromene (CBC), cannabigerol (CBG) and tetrahydrocannabivarin (THCV) botanical drug substances (BDS) on nitrite levels in mouse peritoneal macrophages.

Nitrite Levels:

The levels of nitrites, the stable metabolites of NO, were significantly increased (compared to control) in the medium of macrophages stimulated with LPS (1 µg/ml) for 18 hours with both the isolated phytocannabinoids, as shown in FIG. 3, or the phytocannabinoid BDS, as is shown in FIG. 4.

The test articles were used at non-cytotoxic concentrations as a pre-treatment for 30 min before LPS-stimulation.

All of the test articles resulted in a significant reduction of LPS-stimulated nitrite levels; however THCV and CBG significantly reduced LPS-stimulated nitrite levels. Dexamethasone (1 µM), which is a potent glucocorticoid was used as a positive control.

Conclusion

These data show that isolated THCV, CBG, CBC and CBDV as well as their corresponding BDS, at concentrations which were shown to be not cytotoxic, reduce LPS-stimulated nitrite production in macrophages.

This suggests a potential anti-inflammatory action in intestinal inflammatory disease.

EXAMPLE 2

Effect of Cannabigerol (CBG), Cannabichromene (CBC) and Tetrahydrocannabivarin (THCV) in an Murine Experimental Model of Ulcerative Colitis Materials and Methods Test Articles:

Cannabigerol (CBG), cannabichromene (CBC) and tetrahydrocannabivarin (THCV) were dissolved in ethanol/Tween20/saline. Animals were placed in groups and administered with test article (60 µl per mouse) via IP once daily. Treatment started 3 days before DNBS administration for the preventative treatment experiments or 1 day after DNBS administration for the curative treatments. Test article was administered daily until the sacrifice of the animals, 3 days after DNBS treatment. THCV was only tested for a curative effect.

Induction of Colitis:

Colitis was induced in mice by the intra-colonic administration of DNBS. Briefly, mice were anesthetized and DNBS (8 mg/mouse) was inserted into the colon using a polyethylene catheter (1 mm in diameter) via the rectum (4.5 cm from the anus). Three days after DNBS administration, all animals were euthanized by asphyxiation with $CO_2$. The abdomen was opened by a midline incision and the colon removed, isolated from surrounding tissues, opened along the antimesenteric border, rinsed, weighed, length measured, and processed for evaluations.

The colon weight/colon length ratio activity were determined as index of inflammation. Body weight was also evaluated.

iNOS Expression:

iNOS expression was measured in full-thickness colons from control and DNBS-treated mice by western blot analysis.

Statistical Analysis:

Results are expressed as mean±SEM and analysed with the student's t-test or one-way ANOVA followed by a Turkey-Kramer multiple comparisons test. A P value less than 0.05 was regarded as significant.

Results

Figure 5:
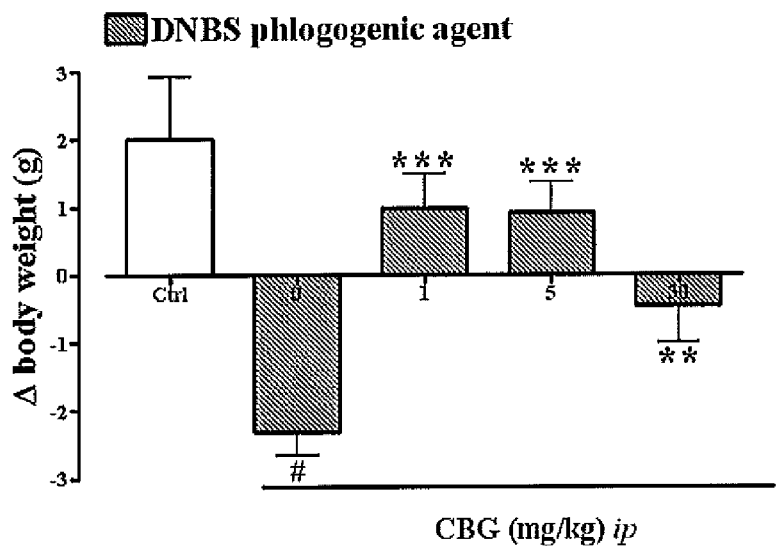
FIG. 5 shows the effect of cannabigerol (CBG) on body weight in DNBS-induced colitis mice.
Figure 5:
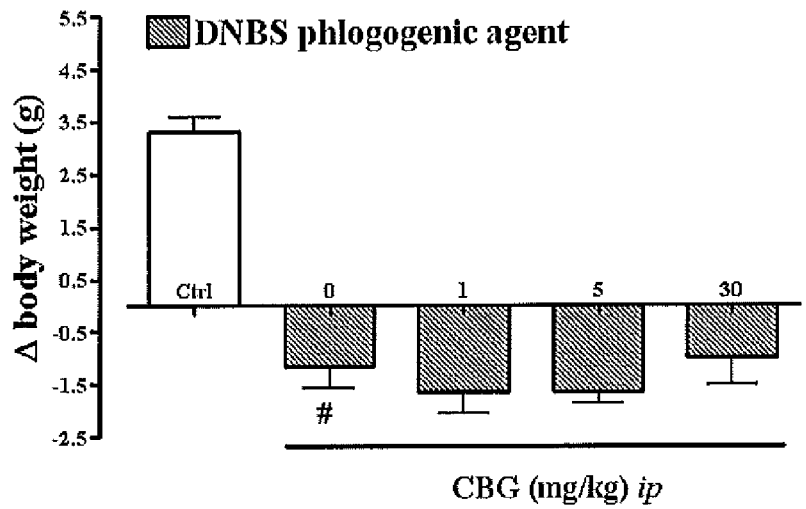

Cannabigerol (CBG):

FIG. 5 demonstrates that pre-treatment with CBG resulted in a highly statistically significant (p<0.001) prevention of the decrease in bodyweight that is associated with the inflammatory response. Treatment after induction of colitis did however not result in a decrease in body weight.

Figure 6:
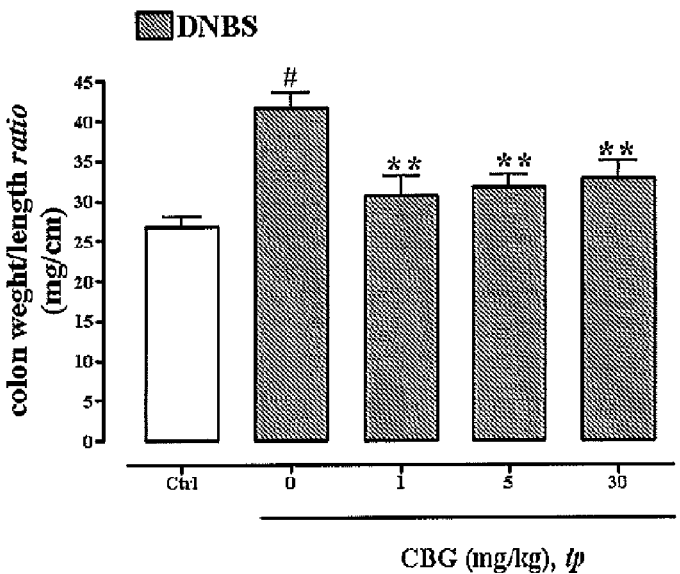
FIG. 6 shows the effect of cannabigerol (CBG) on colon weight:length ratio in DNBS-induced colitis mice.
Figure 6:
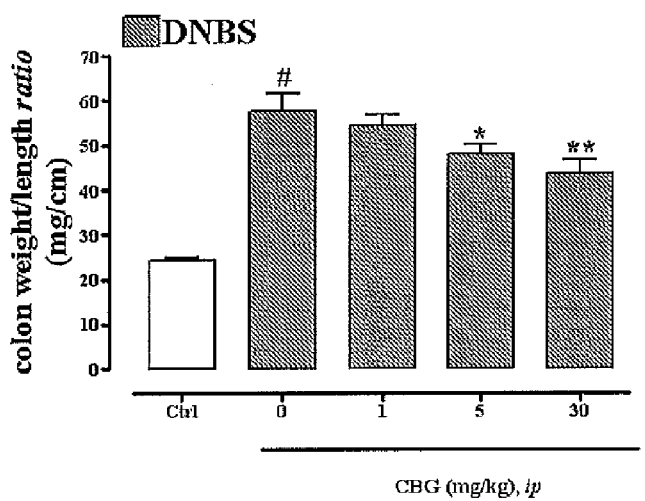

FIG. 6 illustrates that both pre-treatment with CBG and post-treatment with CBG resulted in a significant (p<0.05) reduction of the colon weight:colon length ratio, which is an index of intestinal inflammation, thereby suggesting both a preventative and a curative intestinal anti-inflammatory effect.

Figure 7:
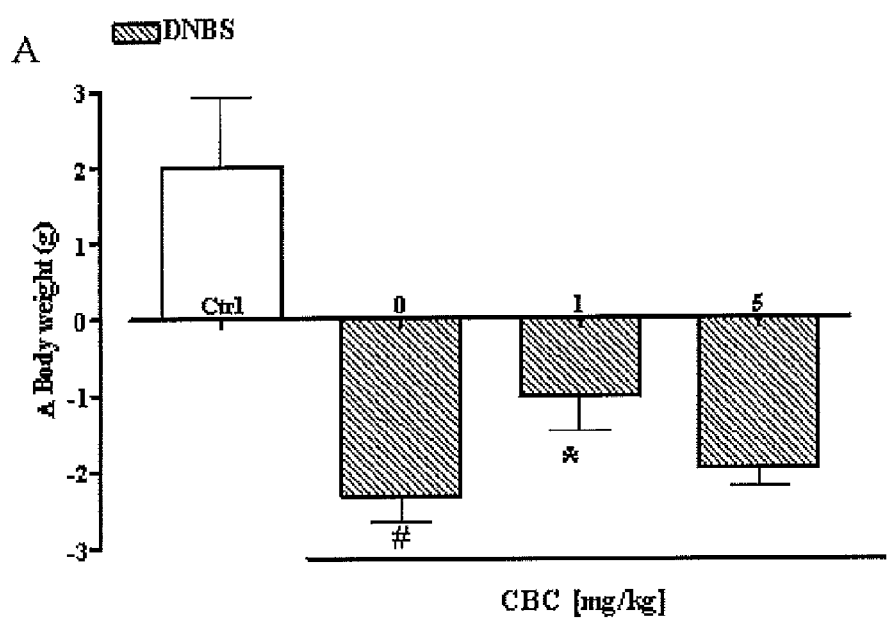
FIG. 7 shows the effect of cannabichromene (CBC) on body weight in DNBS-induced colitis mice.
Figure 7:
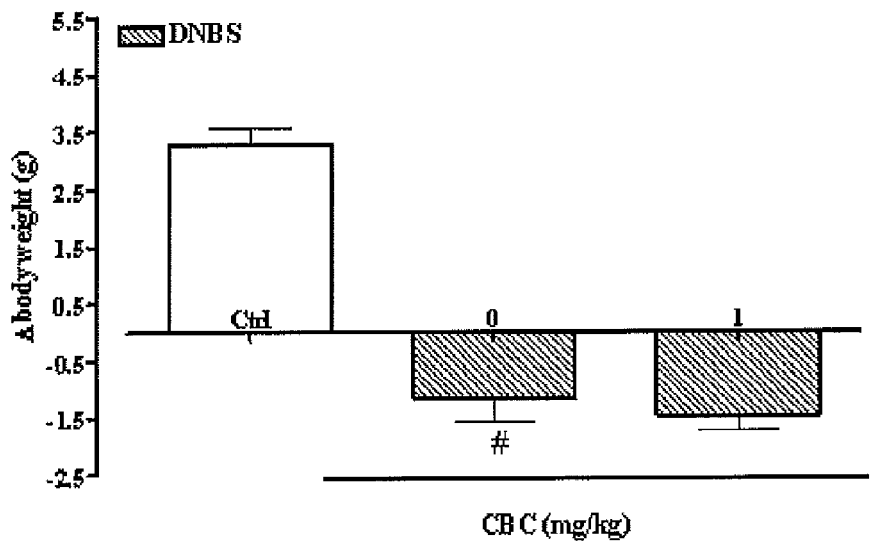

Cannabichromene (CBC):

FIG. 7 demonstrates that pre-treatment with CBC resulted in significant (p<0.05) prevention of the decrease in bodyweight that is associated with the inflammatory response. Treatment with CBC after induction of colitis did not however result in a decrease in body weight.

Figure 8:
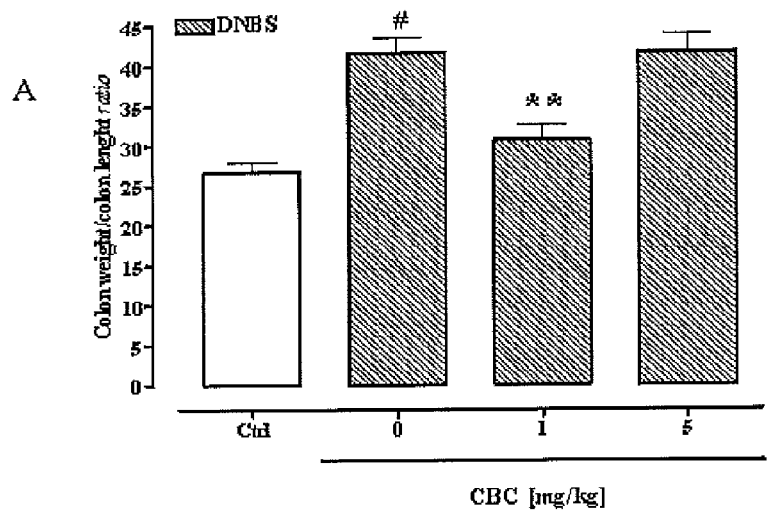
FIG. 8 shows the effect of cannabichromene (CBC) on colon weight:length ratio in DNBS-induced colitis mice.
Figure 8:
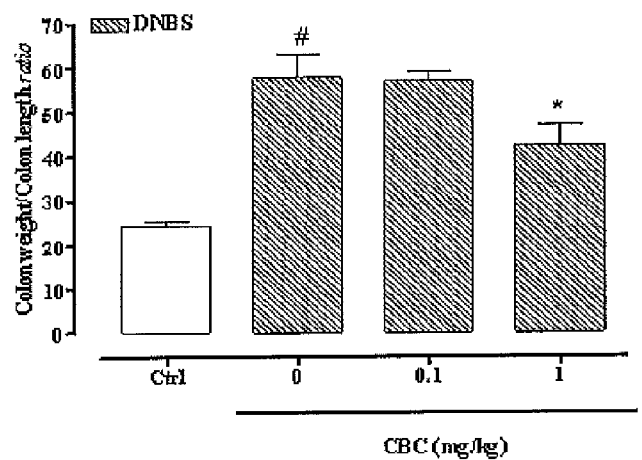

FIG. 8 illustrates that pre-treatment with CBC resulted in a significant (p<0.05) reduction of the colon weight:colon length ratio, which is an index of intestinal inflammation, thereby suggesting a preventative intestinal anti-inflammatory effect. The post-treatment with CBC still resulted in a decrease in the colon weight:length ration however this was not as statistically significant.

Figure 9:
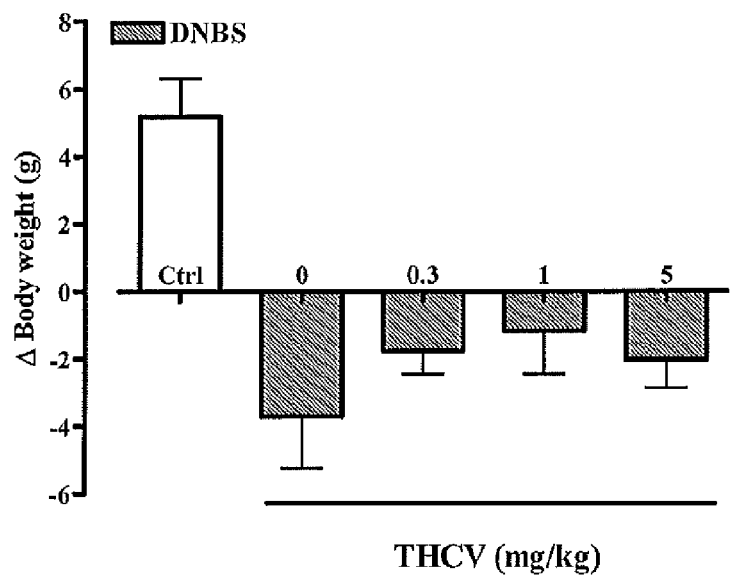
FIG. 9 shows the effect of tetrahydrocannabivarin (THCV) on body weight in DNBS-induced colitis mice.

Tetrahydrocannabivarin (THCV):

FIG. 9 demonstrates that treatment with THCV resulted in a prevention of the decrease in bodyweight that is associated with the inflammatory response, however this decrease was not statistically significant.

Figure 10:
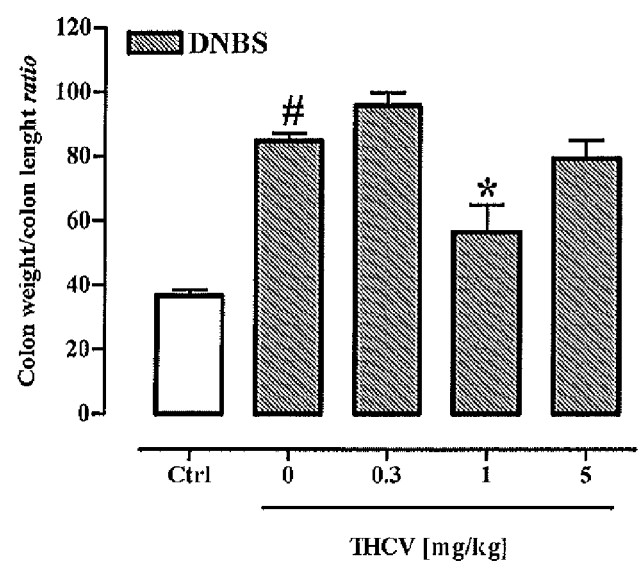
FIG. 10 shows the effect of tetrahydrocannabivarin (THCV) on colon weight:length ratio in DNBS-induced colitis mice.
Figure 11:
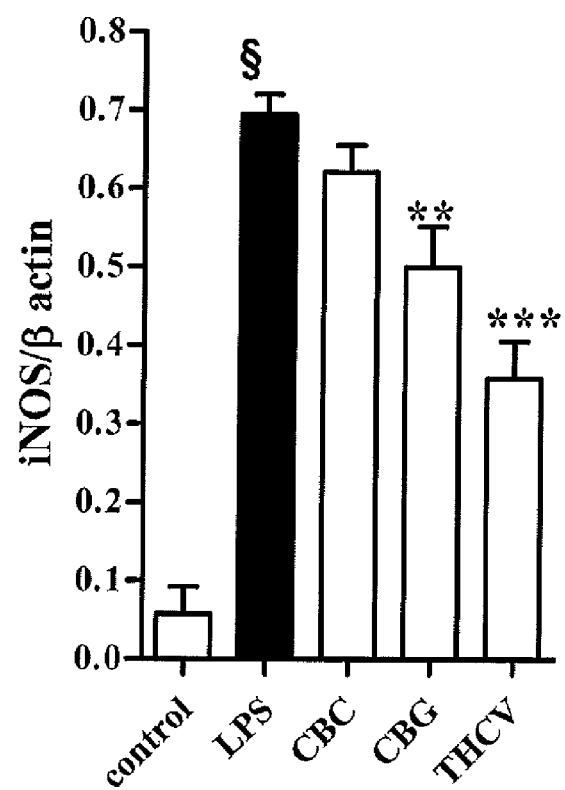
FIG. 11 shows the effect of cannabichromene (CBC), cannabigerol (CBG) and tetrahydrocannabivarin (THCV) on iNOS expression in DNBS-induced colitis mice.

FIG. 10 illustrates that post-treatment with THCV in a significant (p<0.05) reduction of the colon weight:colon length ratio, which is an index of intestinal inflammation, thereby suggesting a curative intestinal anti-inflammatory effect.

iNOS Expression:

FIG. 11 demonstrates that the level of expression of the enzyme inducible nitric oxide synthase (iNOS) in colonic tissues was statistically significantly (p<0.001) lower in the THCV treated animals. This infers that the THCV was able to down regulate the expression of this inflammatory response enzyme.

The level of expression of iNOS in colonic tissues was also statistically significantly (p<0.05) lower in the CBG treated animals. This infers that the CBG was also able to down regulate the expression of this inflammatory response enzyme.

The CBC treated animals did not show a reduction of the expression of iNOS.

Conclusion

Cannabigerol (CBG) has been shown to exert both preventive and curative effects in a murine experimental model of ulcerative colitis and tetrahydrocannabivarin (THCV) has been shown to exert a curative effect in a murine experimental model of ulcerative colitis.

These effects of CBG and THCV are likely to be associated with a down-regulation of the expression of the inflammatory enzyme iNOS which both display.

The phytocannabinoid cannabichromene (CBC) has been shown to exert preventative effect on inflammation.

As such these phytocannabinoids are relevant clinical targets for the treatment of intestinal inflammatory disease.

The invention claimed is:

1. A method for treatment of intestinal inflammatory diseases comprising administering to a subject suffering from intestinal inflammatory disease a therapeutically effective amount of a phytocannabinoid consisting essentially of tetrahydrocannabivarin (THCV).

2. The method as claimed in claim 1, wherein the intestinal inflammatory disease is ulcerative colitis.

3. The method as claimed in claim 1, wherein the intestinal inflammatory disease is Crohn's disease.

4. The method as claimed in claim 1, wherein the THCV is in a synthetic or isolated form.

5. The method as claimed in claim 1, wherein the therapeutically effective amount of THCV is between 1 and 2000 mg.

6. The method as claimed in claim 2, wherein the THCV is in a synthetic or isolated form.

7. The method as claimed in claim 2, wherein the therapeutically effective amount of THCV is between 1 and 2000 mg.

8. The method as claimed in claim 3, wherein the THCV is in a synthetic or isolated form.

9. The method as claimed in claim 3, wherein the therapeutically effective amount of THCV is between 1 and 2000 mg.

\* \* \* \* \*